United States Patent
Krempel et al.

(10) Patent No.: US 6,222,076 B1
(45) Date of Patent: *Apr. 24, 2001

(54) PROCESS FOR THE PREPARATION OF SUBSTITUTED CYCLOKETONES

(75) Inventors: Alfred Krempel, Holzminden; Oskar Koch, Göttingen; Harry Erfurt, Schönhagen, all of (DE)

(73) Assignee: Haarmann & Reimer GmbH, Holxminden (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/215,495

(22) Filed: Dec. 18, 1998

(30) Foreign Application Priority Data

Dec. 23, 1997 (DE) ............................. 197 57 543
Nov. 23, 1998 (DE) ............................. 198 53 862

(51) Int. Cl.$^7$ ................................. C07C 49/21
(52) U.S. Cl. ................ 568/349; 568/343; 568/361; 560/129; 560/248; 560/252
(58) Field of Search .................... 568/342, 343, 568/346, 347, 349, 361; 560/129, 248, 252

(56) References Cited

U.S. PATENT DOCUMENTS 3,856,815   12/1974   Hopp et al. ................ 260/333

*Primary Examiner*—Sreeni Padmanabhan
(74) *Attorney, Agent, or Firm*—Joseph C. Gil; Noland J. Cheung

(57) ABSTRACT

The invention relates to a novel process for the preparation of hydroxyalkyl- and acyloxyalkyl-substituted cycloketones by free-radical addition of hydroxyalkenes and acyloxyalkenes respectively to cyclic ketones.

6 Claims, No Drawings

PROCESS FOR THE PREPARATION OF SUBSTITUTED CYCLOKETONES

FIELD OF THE INVENTION

The present invention relates to a novel process for the preparation of hydroxyalkyl- and acyloxyalkyl-substituted cycloketones by free-radical addition of hydroxyalkenes and acyloxyalkenes respectively to cyclic ketones.

BACKGROUND OF THE INVENTION

The general type of the reaction is already known from DE-B 21 36 496; it is generally carried out in the presence of organic peroxides (e.g. di-tert-butyl peroxide). In this case, the initial charge is for example an excess of cyclododecanone (at least 4 moles per mole of alkene), and to this is added, over the course of 6 hours, a mixture of allyl alcohol and di-tert-butyl peroxide (10–20 mol %, based on alkene) at 140–150° C.

Although, in principle, free-radical reactions of this type take place in a few minutes, with this discontinuous method the allyl alcohol is added very slowly in order to suppress, as far as possible, secondary reactions which lead to polymeric material.

Despite this slow addition, considerable amounts of polymeric byproducts form. A further disadvantage is the poor space-time yield which results because of the long metering time.

The object of the present invention was thus to largely avoid these disadvantages.

DETAILED DESCRIPTION OF THE INVENTION

It has now been possible to achieve the aforementioned object by carrying out the free-radical addition of oxoalkenes to cycloketones in the presence of organic peroxides as free-radical initiators in a continuous process.

Surprisingly, it has been found that by using a continuous procedure, a residence time in the reactor of preferably only from 30 to 80 minutes suffices to obtain a high space-time yield with only small amounts of polymeric byproducts.

The invention thus provides a process for the preparation of compounds of the formula

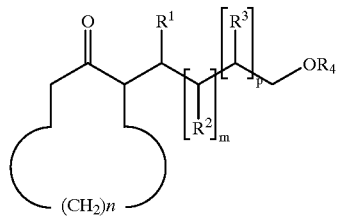

(III)

in which
$R^1$ to $R^3$ independently of one another are hydrogen, methyl or ethyl,
$R^4$ is hydrogen or $C_1$–$C_8$-acyl,
n is an integer from 6 to 10 and
m and p independently of one another are zero or 1, by reacting a cyclic ketone of the formula

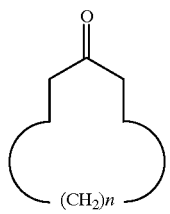

(I)

in which
n is as defined above,
with an alkenol or alkenol ester of the formula

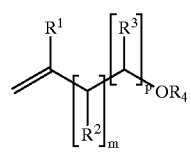

(II)

in which
$R^1$–$R^4$, m, n and p are as defined above,
in the presence of a free-radical initiator, characterized in that the process is carried out continuously.

The following may for example be mentioned as substituted cycloketones according to the invention:

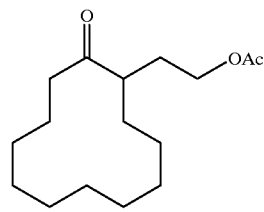

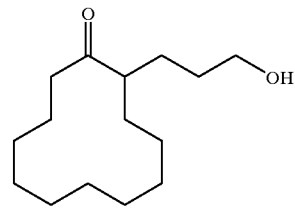

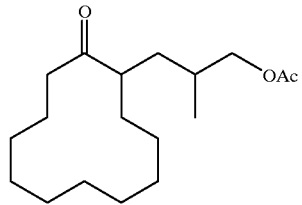

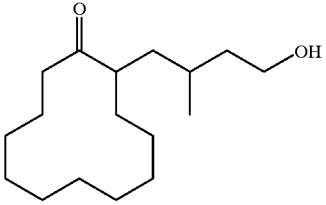

Cyclic ketones for the process according to the invention can for example be the following:

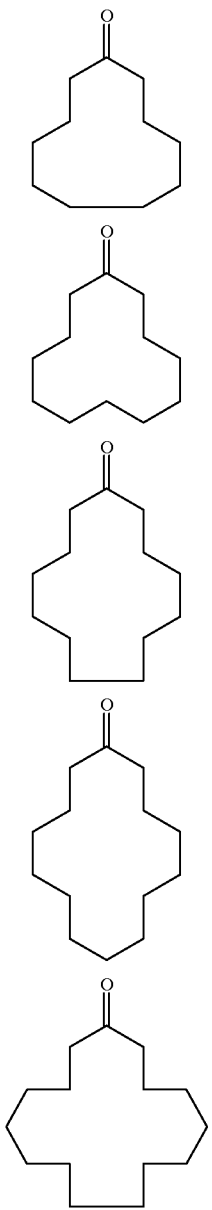

Alkenols for the process according to the invention can for example be the following: vinyl acetate, 2-methyl-2-propen-1-ol, isopropenyl acetate, 3-buten-1-ol, 2-methyl-3-buten-1-ol, allyl alcohol, allyl acetate and 3-methyl-3-buten-ol.

Free-radical initiators for the process according to the invention can for example be the following: cumene hydroperoxide, peroxy esters, such as for example tert.-butyl peroxypivalate, peroxy dicarbonates, such as for example di-(2-ethylhexyl)-peroxydicarbonate, and azo compounds, such as for example 2,2'-azo-bis (4-methoxy-2,4-dimethylvaleronitrile).

The resulting hydroxyalkyl ketones III can be converted, using acid catalysts, to cyclic enol ethers, as are already described in DE-B 21 36 496. These bicyclic enol ethers are in turn very good starting materials for preparing fragrances.

The temperature during the process according to the invention can be from 80 to 200° C., depending on the free-radical initiator used; if the particularly preferred di-tert-butyl peroxide is used, the preferred reaction temperature is from 130 to 1 80° C.

It is advantageous to choose the pressure range such that a homogeneous reaction can take place so that, where appropriate, also readily boiling starting components, such as, for example, allyl alcohol, can be used which have a boiling point below the reaction temperature required for the free-radical initiator. A preferred pressure range is, for example, from 3 to 50 bar. The process is particularly preferably carried out at a pressure of from 10 to 30 bar.

A further advantage of this continuous process is that the excess starting components can be continually distilled off from the product and returned to the reaction process.

In addition, this procedure makes it possible to introduce the starting materials and the catalyst at various positions along the reaction tube in order in this way to vary the procedure depending on the sensitivity and reactiveness of the feed materials or to always keep one component in large excess. This can reduce secondary and consecutive reactions.

The continuous method is associated with a significant increase in the space-time yield; it is thus far superior to the conventional discontinuous process.

EXAMPLE 1

Preparation of 2-(3-hydroxypropyl)cyclododecanone

From a double-walled vessel made of glass, whose temperature is thermostatically controlled at 100° C. and which is fitted with a magnetic stirrer and serves as the storage container for the cyclododecanone, 400 g/h are pumped to a mixing column which is kept at a temperature of 100° C. 21.4 g/h of a mixture of allyl alcohol (12.2 g/h) and di-tert-butyl peroxide (9.2 g/h) are continuously metered into the feedline of the mixing column.

After leaving the mixing column, the reaction mixture flows through a reaction capillary which is 120 m long, has a diameter of 1 mm and has a temperature that is thermostatically controlled at 170° C. A linear rate of 15 cm/sec gives an average residence time of about 40 minutes. Upon leaving the capillary, the reaction mixture flows via a return capillary heated to 100° C. back into the storage vessel. The internal pressure in the reaction capillary is maintained at about 20 bar using a pressure-relief valve.

In the first three hours, this reaction mixture is continuously pumped round, the metering rate of the allyl alcohol/di-tert-butyl peroxide mixture given above being maintained. After this time, a content of hydroxypropylcyclododecanone of about 14% by weight has formed in the reaction mixture.

After these three hours, about 100 g/h of product are then continuously discharged via a needle valve at the end of the reaction capillary, 100 g/h of fresh cyclododecanone being simultaneously fed into the inlet to the mixing column via a further T-piece and, in addition, the metering rate of the allyl alcohol/di-tert-butyl peroxide mixture being reduced to 16.4 g/h (9.4 and 7 g/h respectively). After 7 hours, pumping and discharging are stopped.

Balance after a total reaction time of 10 h:

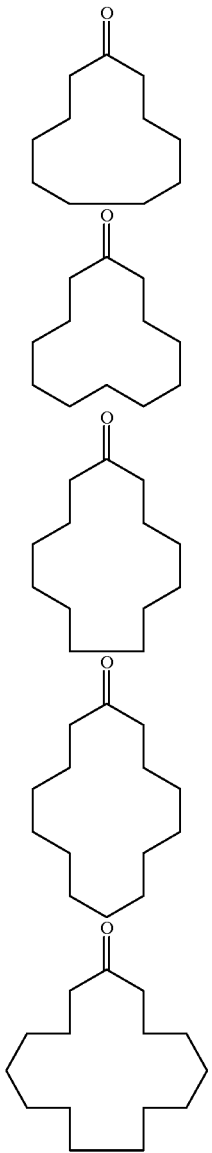

Product content: about 14% by weight=179 g of product
The yield is 42%, based on allyl alcohol.
Comparison (Batch Process)

1 179 g of cyclododecanone are heated to 150° C., and 69 g of allyl alcohol and 31 g of di-tert-butyl peroxide are simultaneously metered in from separate vessels with stirring over the course of 8 hours. When metering is complete, the mixture is then stirred for a further half an hour at the said temperature. The mixture is cooled to give, after a total of 10 hours, 1 279 g of reaction mixture containing 10% of hydroxypropylcyclododecanone.

Balance after a total reaction time of 10 h:

| Feed: | 1179 g (6.48 mol) of cyclododecanone |
| | 69 g (1.19 mol) of allyl alcohol |
| | 31 g (0.21 mol) of di-tert-butyl peroxide |
| Total: | 1279 g of reaction mixture |

Product content: about 10% by weight=128 g of product.
The yield is 45%, based on allyl alcohol.

This comparison shows that the continuous process gives a product yield which is better by a factor of 1.4 after a reaction time of just 10 hours using the same total feed amount of starting materials. Furthermore, the cyclododecanone/allyl alcohol starting material ratio in the continuous process is 3.4:1, compared with 5.5:1 in the batch process, meaning that a clearly smaller excess of cyclododecanone is required. This means, amongst other things, that less cyclododecanone has to be distilled off during work-up.

EXAMPLE 2 TO 6

The above examples were carried out analogously to Example 1:

| Example no. | Substituted cycloketone | cyclic ketone | alkenol | free-radical initiator | yield |
|---|---|---|---|---|---|
| 2 | 2-(2-acetoxy-ethyl)-cyclodo-decanone | cyclodo-decanone | vinyl acetate | di-tert.-butyl peroxide | 50% |
| 3 | 2-(3-acetoxy-2-methylpropyl)-cyclodo-decanone | cyclodo-decanone | isopropenyl acetate | di-tert.-butyl peroxide | 50% |
| 4 | 2-(4-hydroxy-2-methylbutyl)-cyclodo-decanone | cyclodo-decanone | 3-methyl-3-buten-1-ol | azobisiso-butyronitrile | 30% |
| 5 | 2-(3-hydroxy-2-methyl-propyl)-cyclo-undecanone | cycloun-decanone | 2-methyl-2-propen-1-ol | tert.-butyl peroxy-pivalate | 35% |
| 6 | 2-(3-hydroxy-propyl)-cyclo-dodecanone | cyclodo-decanone | allyl alcohol | di(2-ethylhexyl)-peroxy-dicarbonate | 35% |

We claim:
1. Process for the preparation of compounds of the formula

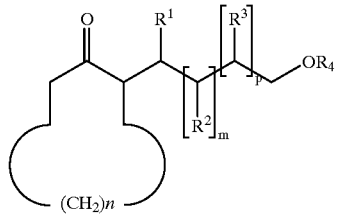

(III)

in which $R^1$ to $R^3$ independently of one another are hydrogen, methyl or ethyl, $R^4$ is hydrogen or $C_1$–$C_8$-acyl, n is an integer from 6 to 10 and m and p independently of one another are zero or 1, by reacting a cyclic ketone of the formula

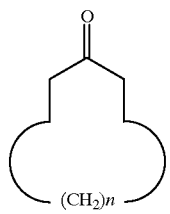

(I)

in which
  n is as defined above,
with an alkenol or alkenol ester of the formula

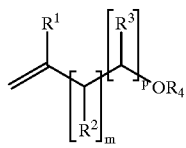

(II)

in which
  $R^1$–$R^4$, m, n and p are as defined above, in the presence of a free-radical initiator, characterized in that the process is carried out continuously.

2. Process according to claim 1, in which the average residence time of the reactants in the reactor is from 30 to 80 minutes.

3. Process according to claim 1, characterized in that the reaction is carried out at a temperature of from 80 to 200° C.

4. Process according to claim 1, characterized in that the reaction is carried out at a pressure of from 3 to 50 bar.

5. Process according to claim 4, characterized in that the reaction is carried out under pressure in a tubular reactor.

6. Process according to claim 1, characterized in that, after the reaction mixture has been obtained, the compound III is separated off and the unreacted starting materials are returned to the reactor.

* * * * *